(12) United States Patent
Desroques et al.

(10) Patent No.: US 8,166,812 B2
(45) Date of Patent: May 1, 2012

(54) VIBRATING WIRE VISCOMETERS

(75) Inventors: Emmanuel Desroques, Paris (FR); Sophie Nazik Godefroy, Cairo (EG); Anthony Robert Holmes Goodwin, Sugar land, TX (US); Christopher Harrison, Auburndale, MA (US); Kai Hsu, Sugar Land, TX (US); Noriyuki Matsumoto, Yokohama (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 335 days.

(21) Appl. No.: 12/578,587

(22) Filed: Oct. 14, 2009

(65) Prior Publication Data

US 2011/0083501 A1    Apr. 14, 2011

(51) Int. Cl.
*E21B 49/08* (2006.01)
*G01N 11/10* (2006.01)
*G01N 29/00* (2006.01)

(52) U.S. Cl. .............. 73/152.28; 73/54.41; 73/64.53
(58) Field of Classification Search .............. 73/54.01, 73/54.23–54.27, 54.41, 64.53, 704
See application file for complete search history.

(56) References Cited

U.S. PATENT DOCUMENTS

| | | | |
|---|---|---|---|
| 4,372,164 A * | 2/1983 | Brown et al. | 73/704 |
| 4,860,581 A | 8/1989 | Zimmerman et al. | |
| 4,936,139 A | 6/1990 | Zimmerman et al. | |
| 5,565,620 A * | 10/1996 | Bohlin | 73/54.25 |
| 5,837,885 A * | 11/1998 | Goodbread et al. | 73/32 A |
| 7,194,902 B1 | 3/2007 | Goodwin et al. | |
| 7,222,671 B2 | 5/2007 | Caudwell et al. | |
| 7,526,953 B2 | 5/2009 | Goodwin et al. | |
| 7,574,898 B2 | 8/2009 | Harrison et al. | |
| 2006/0137873 A1* | 6/2006 | Caudwell et al. | 166/252.5 |

* cited by examiner

*Primary Examiner* — John Fitzgerald
(74) *Attorney, Agent, or Firm* — Jianguang Du; Jody DeStefanis; Jeff Griffin

(57) ABSTRACT

Vibrating wire viscometers are disclosed. An example apparatus to determine the viscosity of a downhole fluid is described, the apparatus including a wire to be immersed in a downhole fluid, to vibrate when an alternating current is applied to the wire within a magnetic field, and to generate an electromotive force when vibrating within the magnetic field, the wire comprising a first resistance. The apparatus further includes a nulling circuit coupled to the wire, wherein the nulling circuit comprises a second resistance that is selectable to be substantially equal to the first resistance, and an analyzer coupled to the wire and the nulling circuit to determine the first resistance, the second resistance, and a viscosity of the downhole fluid based on the first and second resistances, at least one characteristic of the wire, and the electromotive force.

20 Claims, 6 Drawing Sheets

VIBRATING WIRE VISCOMETERS

FIELD OF THE DISCLOSURE

This disclosure relates generally to measuring viscosities of downhole fluids and, more particularly, to vibrating wire viscometers that may be used to measure viscosities of downhole fluids.

BACKGROUND

In the field of downhole petroleum and natural gas exploration, fluid property measurement under native or in situ conditions is an important tool to surveyors to understand the economic viability of a subterranean formation reservoir. Among the fluid properties of interest is viscosity. Viscosity measurements may be performed by exposing a wire to a downhole fluid to be measured and causing the wire to vibrate within the fluid. By measuring the loading effects of the fluid on the vibration of the wire, the viscosity of the downhole fluid may be determined.

Further information on vibrating wire viscometer operation may be found in the following U.S. Pat. Nos. 7,526,953, entitled Methods and Apparatus for the Downhole Characterization of Formation Fluids, by Hegeman, et al.; U.S. Pat. No. 7,574,898, entitled A Vibrating Wire Viscosity Sensor, by Harrison, et al.; U.S. Pat. No. 7,194,902, entitled Apparatus and Method for Formation Evaluation, by Hsu, et al.; and U.S. Pat. No. 7,222,671, entitled Apparatus and Method for Formation Evaluation, by Trusler, et al.

SUMMARY

Vibrating wire viscometers are described below. In an example, an apparatus to determine the viscosity of a downhole fluid may include a wire comprising a first resistance to be immersed in a downhole fluid, to vibrate at a natural or resonance frequency when an alternating current is applied to the wire within a magnetic field, and to generate an electromotive force when vibrating within the magnetic field. The apparatus may further include a nulling circuit coupled to the wire, wherein the nulling circuit comprises a second resistance that is selectable to be substantially equal to the first resistance, and an analyzer coupled to the wire and the nulling circuit to determine the first resistance, the second resistance, and a viscosity of the downhole fluid based on the first and second resistances, at least one characteristic of the wire, and the electromotive force.

In another example, an apparatus to determine the viscosity of a downhole fluid may include a wire comprising a resistance to be immersed in a downhole fluid, to vibrate when an alternating current is applied to the wire within a magnetic field, and to generate an electromotive force when vibrating within the magnetic field. The apparatus may also include a nulling circuit coupled to the wire to generate an offset signal, and an analyzer coupled to the wire and the nulling circuit to determine an offset voltage based on the resistance, to configure the offset signal based on the offset voltage, and to determine a viscosity of the downhole fluid based on the resistance, the offset signal, at least one characteristic of the wire, and the electromotive force.

An example method to measure a viscosity of a downhole fluid is also described. The example method may include immersing a wire in a downhole fluid, determining at least one of a resistance or an offset voltage on the wire, and configuring a nulling circuit to compensate for the resistance or the offset voltage. The example method may further include applying an alternating current to cause the wire to vibrate at a resonance frequency while the wire is subjected to a magnetic field, and determining a voltage on the wire during vibration of the wire by determining a difference between a first signal generated by the alternating current and the magnetic field at the wire and a second signal generated by the nulling circuit.

DETAILED DESCRIPTION

Figure 2:
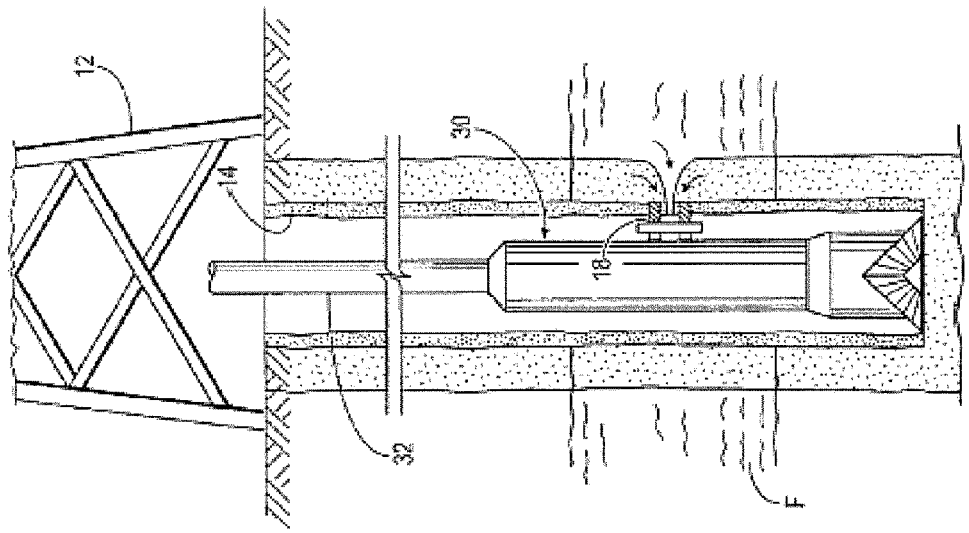
FIG. 2 depicts a drilling tool that may employ the example viscometers described herein.

Certain examples are shown in the above-identified figures and described in detail below. In describing these examples, like or identical reference numbers are used to identify common or similar elements. The figures are not necessarily to scale and certain features and certain views of the figures may be shown exaggerated in scale or in schematic for clarity and/or conciseness. Accordingly, while the following describes example systems, persons of ordinary skill in the art will readily appreciate that the examples are not the only way to implement such systems.

Different aspects and/or features of the example vibrating wire viscometers are described herein. Many of these different aspects and/or features may be combined to realize the respective advantages of these aspects and/or features. Different applications and implementations of the vibrating wire viscometers described herein may benefit from some combination of the below-described features compared to other combinations.

The example vibrating wire viscometers described herein may be used to measure the viscosity of a downhole fluid. In particular, the example vibrating wire viscometers described below may be used to facilitate measurement of downhole fluids having high viscosities that may be very difficult to measure using conventional or known techniques. In some examples, a viscometer includes a sensing wire to be immersed in a downhole fluid to be measured. The sensing wire vibrates at a resonance frequency when exposed to an alternating excitation or actuation current and a magnetic field orthogonal to the wire. When the sensing wire vibrates, a motional electromotive force (emf) is generated on the sensing wire. An analyzer detects or measures the motional emf and can determine the viscosity of the downhole fluid with working equations obtained by solution of the Navier-Stokes equations, based on the induced motional emf, and one or more characteristics of the sensing wire.

The sensing wire also has a finite resistance that causes a resistive voltage drop along the sensing wire. The resistive voltage drop may affect the accuracy of the analyzer measuring the motional emf on the sensing wire as it vibrates. Therefore, in some examples, the analyzer measures the resistive voltage drop on the sensing wire prior to measuring a signal on the sensing wire. After measuring the resistive voltage drop and the signal on the sensing wire, the analyzer may determine the motional emf of the sensing wire as it vibrates and, thus, the viscosity of the downhole fluid.

In some other examples, the vibrating wire viscometer includes a nulling circuit to match the resistance of the sensing wire. An example nulling circuit includes a first resistive element having a fixed resistance and a second resistive element having a variable resistance. Prior to measuring the viscosity of the downhole fluid, the sensing wire resistance is measured and the resistance of the nulling circuit is tuned or adjusted to substantially match the measured resistance of the sensing wire. An analyzer then measures the motional emf by applying the alternating current equally to the sensing wire and the nulling circuit and determining a signal difference between the sensing wire and the nulling circuit.

In some other examples, the nulling circuit includes a reference wire in addition to the sensing wire. The reference wire, which is not exposed to a magnetic field, may have substantially identical electrical characteristics as the sensing wire to provide an offset reference. By determining the difference between the signals on the sensing and reference wires, the motional emf on the vibrating sensing wire and, thus, the viscosity of the downhole fluid may be determined.

In still other examples, the nulling circuit includes active components such as a voltage source and a signal multiplier. The nulling circuit provides an offset signal that may be calibrated prior to the viscosity measurement. To calibrate the offset signal, an analyzer determines the offset voltage or signal at the sensing wire by measuring the sensing wire at a frequency other than the resonance frequency of the wire. This determined or measured offset voltage may then be used to set an offset voltage of the nulling circuit. The analyzer may subtract the offset signal from the measured signal on the sensing wire when measuring the motional emf at the resonance frequency. The difference in the offset signal and the vibration signal may then be used to calculate the viscosity of the measured fluid.

Figure 1:
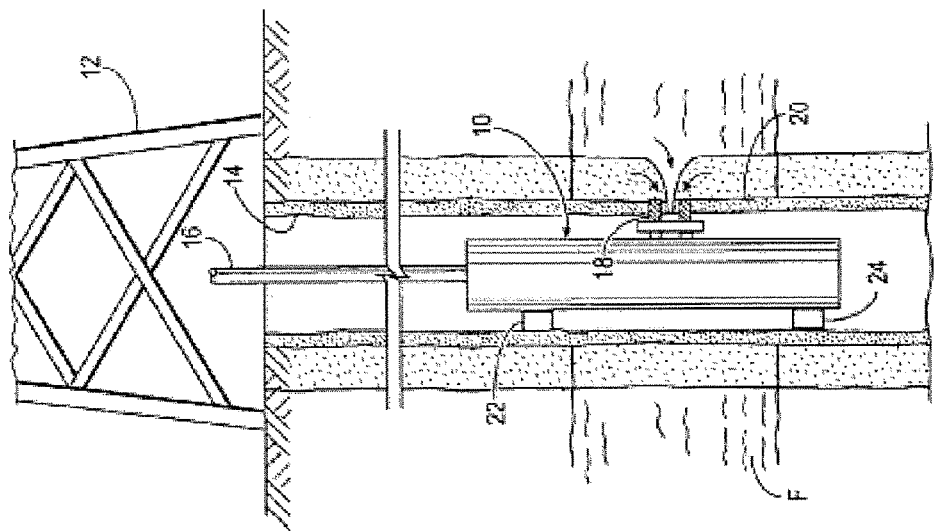
FIG. 1 depicts a wireline tool that is suspended from a rig into a wellbore and which may employ the example viscometers described herein.

FIG. 1 depicts a downhole tool 10, which is suspended from a rig 12 in a wellbore 14 and which may employ the example viscometers described herein. The downhole tool 10 can be any type of tool capable of performing formation evaluation and testing, and may be conveyed by wireline, drillstring, coiled tubing, or slickline. The downhole tool 10 of FIG. 1 is a conventional wireline tool deployed from the rig 12 in the wellbore 14 via a wireline cable 16 and positioned adjacent to a formation F. The downhole tool 10 is provided with a probe 18 adapted to seal against a wall 20 of the wellbore 14 (hereinafter referred to as a "wall 20" or "wellbore wall 20") and draw fluid from the formation F into the downhole tool 10 as depicted by the arrows. Backup pistons 22 and 24 assist in pushing the probe 18 of the downhole tool 10 against the wellbore wall 20. Additionally or alternatively, other types of sealing devices, such as dual, packers, may be used to channel formation fluid into the downhole tool 10 as described in U.S. Pat. No. 4,860,581.

FIG. 2 depicts another downhole tool 30 constructed in accordance with the present disclosure. The downhole tool 30 of FIG. 2 is a drilling tool, which can be conveyed among one or more (or itself may be) a measurement-while-drilling (MWD) drilling tool, a logging-while-drilling (LWD) drilling tool, or other drilling tool known to those skilled in the art. The downhole tool 30 is attached to a drillstring 32 driven by the rig 12 to form the wellbore 14. The downhole tool 30 includes the probe 18 adapted to seal against the wall 20 of the wellbore 14 to draw fluid from the formation F into the downhole tool 30 as depicted by the arrows.

Figure 3:
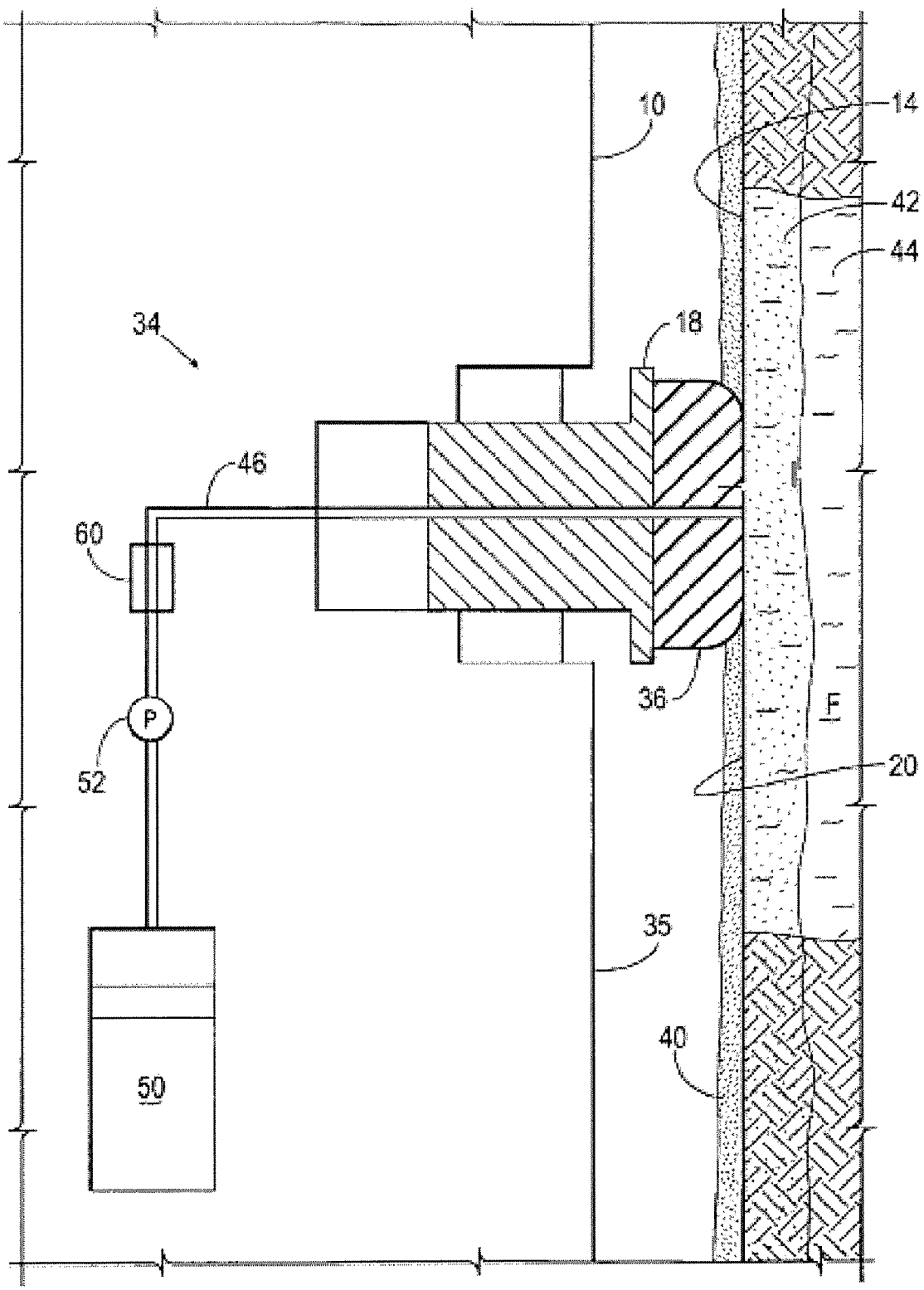
FIG. 3 is a schematic view of a portion of the downhole tool of FIG. 1 depicting a fluid sampling system.

FIG. 3 is a schematic view of a portion of the downhole tool 10 of FIG. 1 depicting a fluid sampling system 34. The probe 18 is preferably extended from a housing 35 of the downhole tool 10 for engagement with the wellbore wall 20. The probe 18 is provided with a packer 36 for sealing against the wellbore wall 20. The packer 36 contacts the wellbore wall 20 and forms a seal with a mud cake 40 lining the wellbore 14. Portions of the mud seep into the wellbore wall 20 and create an invaded zone 42 about the wellbore 14. The invaded zone 42 contains mud and other wellbore fluids that contaminate the surrounding formations, including the formation F and a portion of the virgin fluid 44 contained therein.

The probe 18 is preferably provided with an evaluation flowline 46. Examples of fluid communication devices, such as probes and dual packers, used for drawing fluid into a flowline are depicted in U.S. Pat. Nos. 4,860,581 and 4,936,139.

The evaluation flowline 46 extends into the downhole tool 10 and is used to pass fluid, such as the virgin fluid 44 into the downhole tool 10 for testing and/or sampling. The evaluation flowline 46 extends to a sample chamber 50 for collecting samples of the virgin fluid 44 or may be redirected to discard the sample into the borehole via an exit valve (not shown). A pump 52 may be used to draw fluid through the flowline 46.

While FIG. 3 shows a sample configuration of a downhole tool used to draw fluid from a formation, it will be appreciated by one of skill in the art that a variety of configurations of probes, flowlines and downhole tools may be used and is not intended to limit the scope of the invention.

In accordance with the present disclosure, a viscometer 60 is associated with an evaluation cavity within the downhole tool 10, such as the evaluation flowline 46 for measuring the viscosity of the fluid within the evaluation cavity. Example implementations of the viscometer 60 are shown in more detail in connection with FIGS. 4-9.

The downhole tool 30 of FIG. 2 may also be provided with the housing 35, the probe 18, the fluid flow system 34, the packer 36, the evaluation flowline 46, the sample chamber 50, the pump(s) 52 and the viscometer(s) 60 in a similar manner as the downhole tool 10.

A vibrating wire viscometer (e.g., the viscometer 60) typically includes a sensing wire held in tension between two clamps. The sensing wire is caused to vibrate by passing through the sensing wire an alternating excitation or actuation current (AC) signal having a fixed amplitude while the sensing wire is within or exposed to a magnetic field or flux. A voltage V is generated across the sensing wire in response to the AC signal and the magnetic field. The voltage V can be expressed as $V=V_1+V_2$, where the term $V_1$ represents a voltage drop due to the electrical impedance of the sensing wire, which is substantially resistive, and where the term $V_2$ represents an induced or motional voltage drop or emf due to the motion of the sensing wire in the magnetic flux. The term $V_1$ (also referred to herein as the offset voltage or signal) may include background noise such as electrical cross-talk and other forms of electrical coupling, and may be described as shown in Equation 1.

$$V_1 = a + bf + i(c + df) \quad \text{(Eq. 1)}$$

In Equation 1, f is the resonance frequency of the sensing wire in the fluid under test and a, b, c, and d are resistive and reactive parameters that may be determined experimentally. In some examples, a, b, c, and d are estimated by performing a nonlinear regression based on V. The induced or motional voltage $V_2$ may be expressed as shown in Equation 2.

$$V_2 = \frac{i\Lambda f}{f_0^2 - (1+\beta)f^2 + i(\beta' + 2\Delta_0)f^2} \quad \text{(Eq. 2)}$$

In Equation 2, the term $f_0$ represents the resonance frequency of the sensing wire in a vacuum, $\Delta_0$ is the damping factor due to internal losses, $\Lambda$ is the permeance of the sensing wire, and $\beta$ and $\beta'$ are the inertia and damping of the wire, respectively. The term $\beta$ may be expressed as shown in Equation 3, and the term $\beta'$ may be expressed as shown in Equation 4.

$$\beta = k\frac{\rho}{\rho_s} \quad \text{(Eq. 3)}$$

$$\beta' = k'\frac{\rho}{\rho_s} \quad \text{(Eq. 4)}$$

In Equations 3 and 4, $\rho$ and $\rho_s$ represent the density of the downhole fluid being measured and the sensing wire, respectively. The term k may be expressed by $k = -1 + 2\text{Im}(A)$, and the term k' may be expressed by $k' = 2\text{Re}(A)$, where Im(A) and Re(A) is the imaginary part and real part of the complex quantity A, respectively. The complex quantity A may be expressed as shown in Equation 5.

$$A = i\left\{1 + \frac{2K_1(\sqrt{i\Omega})}{\sqrt{i\Omega}\, K_0(\sqrt{i\Omega})}\right\} \quad \text{(Eq. 5)}$$

In Equation 5, $K_1$ and $K_0$ are modified Bessel functions of the second kind, of orders 1 and 0, respectively. The term $\Omega$ is a parameter related to the Reynolds number, and is expressed in Equation 6.

$$\Omega = \frac{2\pi f \rho R^2}{\eta} \quad \text{(Eq. 6)}$$

In Equation 6, $\eta$ is the viscosity of the downhole fluid, $\rho$ is the density of the downhole fluid, and R is the radius of the sensing wire.

The foregoing equations are accurate provided the following conditions are satisfied: 1) the radius of the sensing wire is small in comparison to the length of the sensing wire; 2) the compressibility of the downhole fluid being measured is negligible; 3) the radius of the body (e.g., flowline, test chamber) containing the downhole fluid is large in comparison to the sensing wire radius so that fluidic boundary effects are negligible; and 4) the amplitude of oscillation of the sensing wire is small. When these conditions are satisfied, the response of the sensing wire to the viscosity of the downhole fluid may be accurately analyzed and predicted using the foregoing equations.

When the sensing wire is placed in a magnetic field that is perpendicular to the sensing wire, the wire may be driven in steady-state transverse oscillations by passing an AC excitation or actuation current through the wire. The transverse oscillations are caused by the Lorentz force exerted on the sensing wire, which changes the direction (e.g., left to right or right to left) of the sensing wire when the AC current changes the direction (e.g., up to down or down to up). Therefore, the purpose of AC current is to impart mechanical energy to the sensing wire to enable the wire to displace from its neutral position and to thereby enable the wire to vibrate at or about the natural resonant frequency of the wire. The frequency of the AC excitation or actuation current may be fixed at a frequency. However, the natural oscillation frequency of wire may be relatively high and is determined by the characteristics of wire (e.g., tension, wire radius, fluid density, fluid viscosity, etc.). Typically, the resonance frequency of the wire is a few kilohertz (kHz).

According to Faraday's induction law, the oscillation of a wire in a magnetic field induces an emf (i.e., $V_2$) across the sensing wire 402. The recorded measurement data (i.e., $V = V_1 + V_2$) is a complex amplitude (in-phase and quadrature component) and is acquired at multiple frequencies around the resonance frequency of the wire. Therefore, V is a function of frequency (i.e., V(f)), where f is the frequency or frequency range at or near the resonance frequency of wire (as used in Equations 1 to 6).

Figure 4:
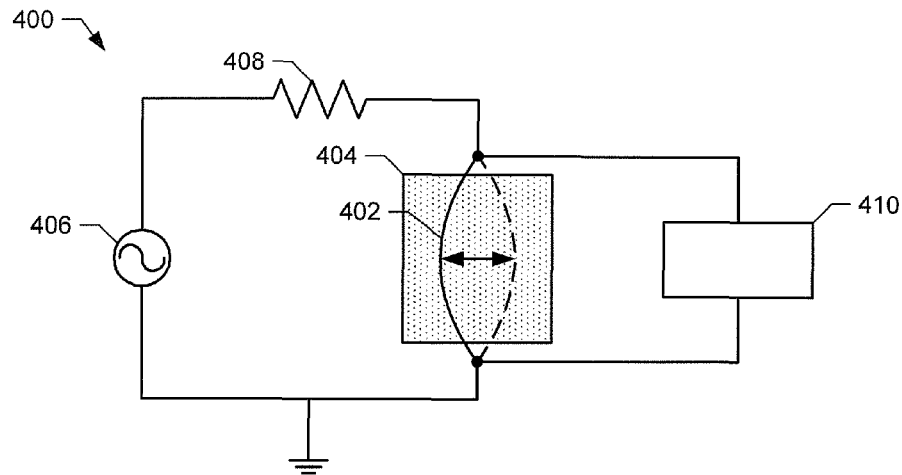
FIG. 4 is a schematic diagram of a conventional vibrating wire viscometer circuit to measure the viscosities of downhole fluids.

FIG. 4 is a schematic diagram of a known vibrating wire viscometer 400 to measure the viscosities of downhole fluids. The viscometer 400 includes a sensing wire 402 immersed in a downhole fluid. The sensing wire 402 is exposed to a magnetic field 404. A signal generator 406 provides an alternating excitation or actuation current to the sensing wire 402. A resistor 408 determines an amount of current applied to the sensing wire 402 as a result of the signal provided by the signal generator 406.

As the signal generator 406 applies the alternating current to the vibrating sensing wire 402 while the magnetic field 404 is present and the sensing wire 402 is immersed in a downhole fluid, the sensing wire 402 vibrates at its resonant frequency and a motional emf is generated across the wire 402 based on the viscosity of the downhole fluid as provided in Equations 2 to 6 above. Generally, as the viscosity of the downhole fluid increases, the motional emf decreases. A measurement device 410 measures the motional emf to determine the viscosity of the downhole fluid in which the sensing wire 402 is immersed.

Figure 5:
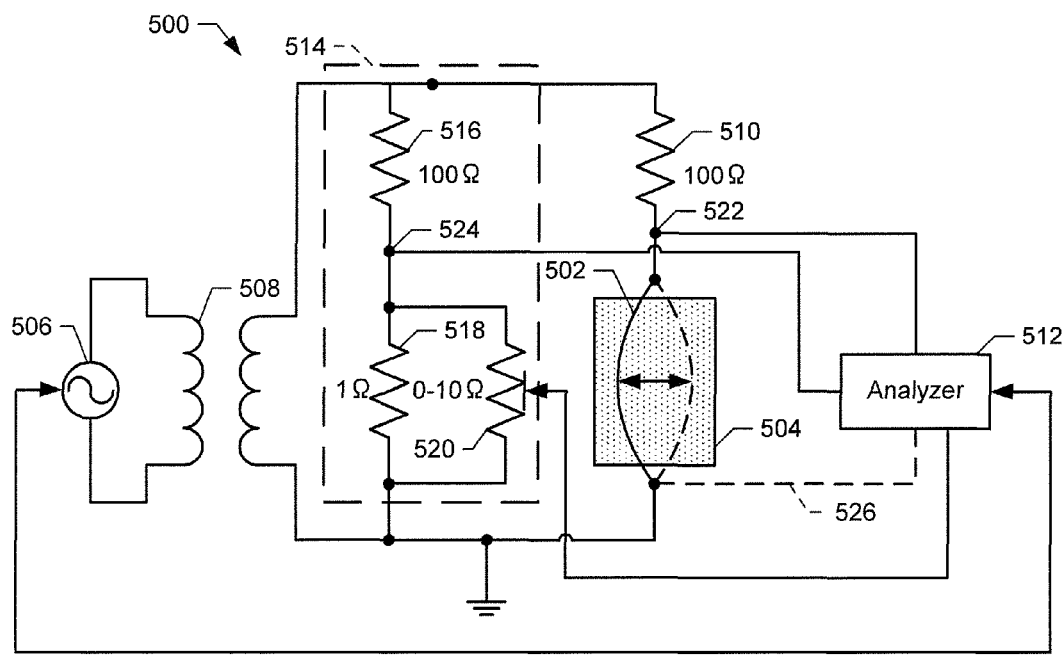
FIG. 5 is a schematic diagram of an example passive vibrating wire viscometer to extend the range of viscosity measurements.

FIG. 5 is a schematic diagram of an example passive vibrating wire viscometer 500 that extends the range of viscosity measurements. The example vibrating wire viscometer 500 may measure downhole fluids having viscosities higher than accurately measurable by the known vibrating wire viscometer 400 of FIG. 4. To measure viscosity, the viscometer 500 includes a sensing wire 502 that may be immersed in a downhole fluid. In some examples, the sensing wire 502 is made of tungsten and is held between two clamps. The dashed line opposite the sensing wire 502 represents the vibration or movement of the sensing wire 502. During measurement, the sensing wire 502 is exposed to a magnetic field 504 oriented orthogonally to the sensing wire 502.

The example viscometer 500 further includes an AC signal generator 506. In the illustrated example, the AC signal generator 506 is coupled to the sensing wire 502 via a transformer 508 to reduce the voltage and increase the current delivered to the sensing wire 502 relative to the AC signal generator 506. However, any pre-amplifier may be used in place of the transformer 508 to generate a desired excitation or actuation current for the sensing wire 502. A current-limiting resistor 510 is also provided to control or limit the voltage and current to the sensing wire 502. The AC signal generator 506, the transformer 508 (or pre-amplifier), and the resistor 510 may be used to provide an AC signal having a desired voltage and current to the sensing wire 502 to improve measurement accuracy.

The example viscometer 500 further includes an analyzer 512 to measure the viscosity of the downhole fluid by determining the motional emf of the wire 502. The analyzer 512 is described in further detail with respect to FIG. 6 below.

As described above, the sensing wire 502 exhibits a resistive voltage $V_1$ when the AC excitation or actuation signal is applied to the sensing wire 502. Generally, the magnitude of the voltage $V_1$ is much greater than the magnitude of the motional emf signal or voltage $V_2$. Also, the AC excitation or actuation signal may have a much lower frequency than the resonance frequency of the sensing wire 502. While the AC excitation signal can be filtered out for measurement of the higher frequency signal(s), the signal $V_1$ can introduce an offset at the measured frequency that may reduce the accuracy of measurements. Because the signal $V_1$ has a significantly larger magnitude than the signal $V_2$, the sensitivity of measurement equipment would be reduced if the contribution of $V_1$ to V was not reduced or substantially eliminated prior to measuring $V_2$. Thus, when attempting to measure $V_2$, analysis of the voltage V involves identifying the signal $V_2$ and filtering out the signal $V_1$. The actuation force of the wire 502 is approximated by Equation 7.

$$F=BIl \qquad (Eq.\ 7)$$

In Equation 7, B is the magnetic flux (e.g., from the magnetic field 504) over a length l of wire (e.g., the sensing wire 502) through which a current I (e.g., the current generated by the AC signal generator 506, the transformer 508, and the resistor 510) flows. The voltage $V_2$ may be expressed as shown in Equation 8.

$$V_2=Balf/(4\pi) \qquad (Eq.\ 8)$$

In Equation 8, a is the amplitude and f is the resonance frequency of the sensing wire 502. In general, the amplitude a is proportional to the actuation force F of Equation 7, and Equation 7 may therefore be substituted into Equation 8 to show that $V_2$ is proportional to $B^2$ and I.

In general, a permanent magnet is more practical for downhole viscosity testing because an electromagnet tends to cause resistive heating, which changes the viscosity of the downhole fluid being measured and, thus, can make accurate measurements of fluid in the downhole environment very difficult. Additionally, few permanent magnetic materials currently exist which are suitable for downhole conditions, including heat and pressure. In the example of FIG. 5, the magnetic field 504 is generated using one or more Samarium Cobalt $Sm_2Co_{17}$ permanent magnets. As a result, B does not change in Equation 8 and cannot be used to increase $V_2$.

While increasing the current I increases the driving force of the sensing wire 502, increasing the current also increases the background or resistive portion of the signal (i.e., $V_1$). For example, a current of 0.1 Amperes (A) across a 0.1Ω resistance of the wire 502 produces a voltage $V_1$ across the sensing wire 502 of 10 millivolts (mV). However, the signal $V_2$ caused by the motion of the wire 502 within the magnetic field 504 may only be about 0.01 mV. Therefore, the motional emf signal may be approximately 1000 times smaller than the background voltage or noise $V_1$. Thus, by increasing the current through the sensing wire 502, the noise $V_1$ increases at a much greater rate than the motional emf signal $V_2$.

Additionally, the resonance of the sensing wire 502 has a quality factor Q, which may be expressed as $Q=E/\Delta E$, where E is the energy stored in the vibrating sensing wire 502 and $\Delta E$ is the energy dissipated by the vibrating sensing wire 502. The stored energy E is proportional to the square of the radius R of the sensing wire 502 ($E \propto R^2$), while the dissipated energy is proportional to the cube root of R ($E \propto R^{1/3}$). Thus, the quality factor increases as the radius is increased $Q \propto R^{5/3}$). For the analyzer 512 to measure the viscosity properly, Q should be greater than or equal to 1.5. Thus, the sensing wire 502 has a lower diameter limit. Increasing the tension applied to the sensing wire 502 may also increase Q. However, increasing the tension on the sensing wire reduces sensitivity to viscosity.

The example viscometer 500 further includes a nulling circuit 514 to null the voltage $V_1$ resulting from the sensing wire 502 impedance. By nulling or reducing the voltage $V_1$, the analyzer 512 can record the motional emf signal or voltage $V_2$ without background interference and thereby increase the signal-to-noise ratio (SNR) to determine the viscosity of the fluid under test. In other words, the magnitude of the motional emf or voltage signal $V_2$ can be increased relative to the noise signal $V_1$. To null the noise voltage $V_1$, the nulling circuit 514 is placed electrically parallel to the sensing wire 502 and the resistor 510 to match the resistances of the sensing wire 502 and the resistor 510 as closely as possible or practical. To this end, the nulling circuit 514 includes a first fixed resistor 516, a second fixed resistor 518, and a potentiometer 520 or other variable resistance. The example fixed resistor 516 has a resistance equal to about 100Ω to substantially match the resistance of the resistor 510. Matching the resistors 510 and 516 causes substantially equal currents to flow through the sensing wire 502 and the nulling circuit 514. To obtain resistance matching for the resistors 510 and 516, high-precision resistors may be used and/or additional resistors and/or potentiometers may be placed in parallel with one or both of the resistors 510 and 516.

The second fixed resistor 518 has a resistance approximately equal to 1Ω. The example potentiometer 520 has a variable resistance that may be adjusted between 0 to approximately 10Ω. The example resistances of the resistor 518 and the potentiometer 520 are based on a sensing wire 502 constructed using tungsten. However, if another material is used, different resistances may be used to implement the resistor 518 and the potentiometer 520.

In operation, the analyzer 512 of FIG. 5 first nulls the resistance of the sensing wire 502 by matching the resistor 518 and potentiometer 520 parallel path resistance to the sensing wire 502 resistance. When the example vibrating wire viscometer 500 is placed in a downhole environment, the temperature of the downhole environment tends to be higher than the temperature at the surface. Like other materials, the resistance of tungsten varies in response to changes in temperature and has a resistance coefficient $dR/dT \approx 0.004\ K^{-1}$. Thus, a change in temperature of 200 K results in an approximately 80% increase in resistance in the sensing wire 502, which causes the nulling circuit 514 to have an incorrect resistance if the resistance change is not compensated. As a result, measurement and tuning of the nulling circuit 514 may be performed at each downhole measurement location to compensate for the changing resistance or offset voltage $V_1$ of the sensing wire 502.

To measure the resistance of the sensing wire 502, the analyzer 512 may measure test signals at a frequency that is substantially different from the resonance frequency of the sensing wire 502 as the AC signal generator 506 delivers a current to the sensing wire 502 at a constant frequency. By measuring the test signals at a frequency other than the resonance frequency, the analyzer 512 may measure the resistance of the sensing wire 502 under actual testing conditions (e.g., at a temperature similar or identical to a downhole temperature) without measuring the motional emf or voltage $V_2$ on the sensing wire 502. After measuring the resistance of the sensing wire 502, the analyzer 512 may adjust the resistance of the potentiometer 520 such that, when in parallel, the resistances of the resistor 518 and the potentiometer 520 are equal or substantially equal to the resistance of the sensing wire 502.

To measure the viscosity, the analyzer 512 measures the difference between the voltage signal across the sensing wire 502 (e.g., at node 522) and the voltage signal across the resistor 518 and potentiometer 520 (e.g., at node 524). The signal at the node 522 is equal to $V_1+V_2$, and the signal at the node 524 is equal to $V_1$. Thus, the analyzer 512 may determine the motional emf or voltage signal component $V_2$ by measuring the difference between the signals at the nodes 522 and 524. Additionally or alternatively, the example analyzer 512 may measure the signals at both of the nodes 522 and 524 relative to a reference signal (e.g., a ground reference) and subtract the signal across the nulling circuit 514 from the signal across the sensing wire 502. The dashed line 526 from the analyzer 512 to the ground reference illustrates an example connection to measure the signals at the nodes 522 and 524 relative to a reference signal or voltage.

Figure 6:
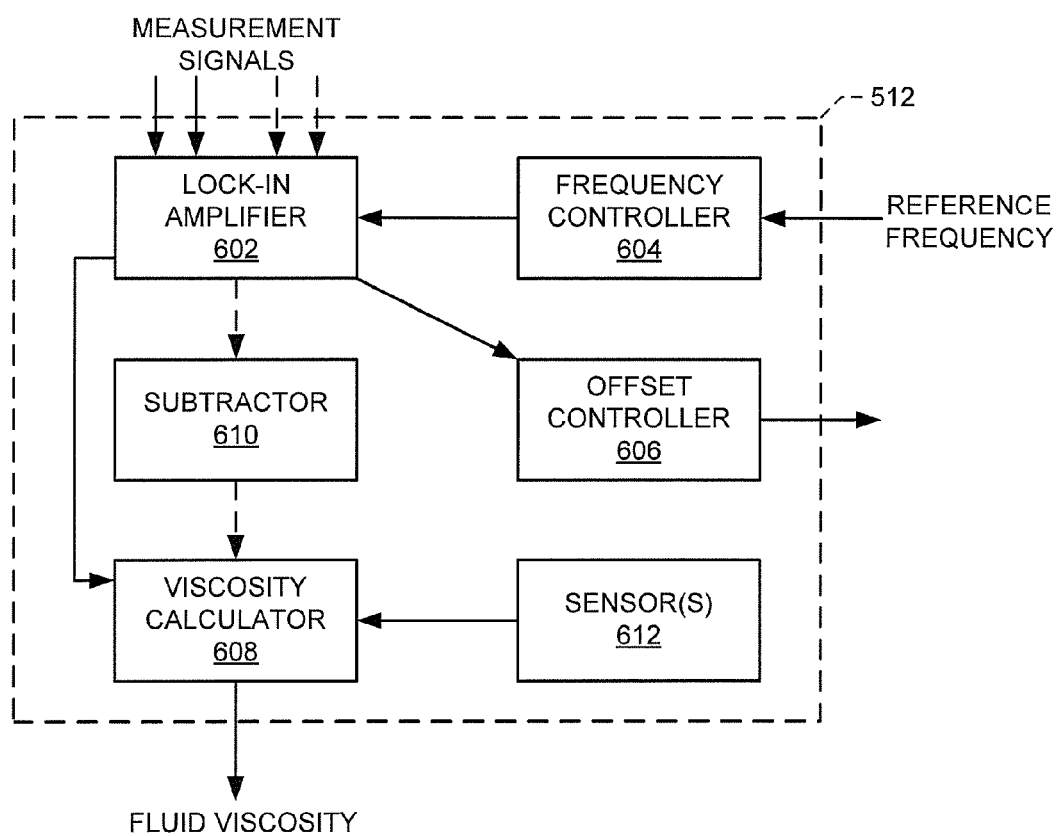
FIG. 6 is a more detailed block diagram of the example analyzer illustrated in FIG. 5.

FIG. 6 is a more detailed block diagram of the example analyzer 512 illustrated in FIG. 5. As described above, the analyzer 512 may be used to measure a motional emf or voltage (e.g., $V_2$) on a vibrating sensing wire (e.g., the sensing wire 502 of FIG. 5) during viscosity testing. In general, the analyzer 512 measures the resistance of and/or offsets the resistive voltage $V_1$ of the wire 502, measures the motional emf or voltage $V_2$, and determines the viscosity of the downhole fluid based on the motional emf or voltage $V_2$. The analyzer 512 may be located downhole near the sensing wire 502, at a surface location, or any other location where the analyzer 512 may be in electrical communication with the vibrating wire viscometer 500 without compromising measurement accuracy.

To measure the resistance of the wire 502, the example analyzer 512 includes a lock-in amplifier 602 and a frequency controller 604. As described in more detail below, the lock-in amplifier 602 can determine the amplitude of a signal through background noise, given the frequency of the signal. To prevent any motional emf $V_2$ on the sensing wire 502 from interfering with a resistance or offset measurement, the frequency controller 604 causes the lock-in amplifier 602 to measure frequencies around the resonance frequency of the sensing wire 502. The frequency controller 604 determines frequencies to be scanned by the lock-in amplifier 602. For example, if the resonance frequency of the sensing wire 502 is 1 kHz, the frequency controller 604 may cause the lock-in amplifier 602 to measure the complex amplitudes (i.e., in-phase and quadrature components) of the signal across the sensing wire 502 between 980 Hz and 1020 Hz at 1 Hz intervals. The complex amplitude corresponds to V, from which $V_1$ may be subtracted as described below to obtain $V_2$.

The lock-in amplifier 602 receives the test measurement frequency (e.g., from the frequency controller 604) and measurements from the measurement point(s). For example, the lock-in amplifier 602 may receive a measurement from the node 522 (FIG. 5) relative to a ground reference (i.e., the voltage across the sensing wire 502). In the example viscometer 700 of FIG. 7, no resistance measurement such as noted above is needed because the resistance of the reference wire 702 may be subtracted from the signal on the sensing wire 502 during the measurement process.

After the resistance and/or offset voltage on the wire 502 is determined, the lock-in amplifier 602 provides the measured resistance and/or offset voltage to an offset controller 606, which controls the nulling circuit 514. For example, in FIG. 5, the analyzer 512 (e.g., via the offset controller 606) adjusts the variable resistance of the potentiometer 520.

The lock-in amplifier 602 (also known as a phase-sensitive detector) is used to detect and measure small AC signals in the presence of relatively large noise (i.e., a condition corresponding to a relatively small SNR). The lock-in amplifier 602 receives an external reference frequency $f_{ref}$ (e.g., from the frequency controller 604) and measures a signal component within a specified bandwidth of the external reference frequency $f_{ref}$ to the relative exclusion of other frequencies. The lock-in amplifier 602 generates an internal reference signal based on the external reference frequency. When receiving a signal to measure having a frequency $f_{sig}$ (e.g., the signal $V=V_1+V_2$ across the sensing wire 502), the lock-in amplifier 602 amplifies the input signal, multiplies the amplified input signal by the internal reference frequency $f_{ref}$, and passes the result through a low-pass filter.

The result of the multiplication is two AC signals at two frequencies based on the signal frequency $f_{sig}$ and the reference frequency $f_{ref}$. For example, the frequencies may be $(f_{sig}+f_{ref})$ and $(f_{sig}-f_{ref})$. The lock-in amplifier 602 filters out AC signals via a low-pass filter, but in the case where $f_{sig}=f_{ref}$, one of the AC signals becomes a DC signal because the frequency $(f_{sig}-f_{ref})$ is zero. Therefore, the low pass filter does not filter out the DC signal and the lock-in amplifier 602 outputs a DC signal having an amplitude proportional to the amplitude of the signal to be measured. The amplitude of the input signal (e.g., the motional emf $V_2$) may then be determined according to Equation 9.

$$V_2 = \frac{2V_O}{V_{LI}\cos(\theta_2 - \theta_{LI})} \quad \text{(Eq. 9)}$$

In Equation 9, $V_O$ is the amplitude of the lock-in amplifier output (i.e., output from the low-pass filter), $V_{LI}$ is the amplitude of the lock-in amplifier internal reference signal, $\theta_2$ is the phase of the input signal (e.g., $V_2$), and $\theta_{LI}$ is the phase of the lock-in amplifier internal reference signal. $V_{LI}$ is known, and $(\theta_2-\theta_{LI})$ may be measured by the lock-in amplifier 602.

While the lock-in amplifier 602 can attenuate noise outside of the measured bandwidth, noise within the measured bandwidth, and especially noise at the reference frequency (e.g., the resonance frequency), passes through with no attenuation. Thus, the voltage $V_1$ also passes through the lock-in amplifier 602 and is amplified in addition to $V_2$. By eliminating or substantially reducing $V_1$, the sensitivity of the lock-in amplifier 602 may be increased and the signal $V_2$ may be measured more easily. Increasing the sensitivity of the lock-in amplifier 602 may include increasing pre-amplification of the motional emf $V_2$ and the white noise within the measured bandwidth. If the signal $V_1$ were not substantially eliminated or reduced, $V_1$ would substantially limit the pre-amplification of the signal to the limits of the lock-in amplifier 602 range because $V_1$ is much larger than $V_2$. As described above, the example viscometer 500 of FIG. 5 (e.g., via the nulling circuit 514) substantially eliminates $V_1$ to increase the relative magnitude of $V_2$.

In the example of FIG. 5, the analyzer 512 (e.g., via the lock-in amplifier 602) measures the signal at the node 522 relative to the node 524. Thus, the signal $V_1$ is nulled or negated by integrating $V_1$ into a common reference signal. Because the larger signal, $V_1$, is nulled, the sensitivity (e.g., amplification) of the lock-in amplifier 602 may be increased to more easily identify $V_2$ within the remaining noise of the measured bandwidth.

When the lock-in amplifier 602 has measured the signal $V_2$, the signal $V_2$ is passed to a viscosity calculator 608. In some examples described below, the lock-in amplifier 602 may pass measured signals to a subtractor 610 for further processing to obtain the signal $V_2$. The operation of the subtractor 610 is described in more detail below with respect to FIGS. 7 and 8. However, the subtractor 610 is not used when the analyzer 512 is applied to the example of FIG. 5.

The viscosity calculator 608, given $V_2$, determines the viscosity of the downhole fluid within which the sensing wire 502 vibrates during measurement. Using Equations 2 to 6 defined above, the viscosity calculator 608 may determine the viscosity ($\eta$) of the downhole fluid. Because the Equations 2 to 6 require additional information to determine the viscosity, the example analyzer 512 also includes one or more sensor(s) 612. The sensors 612 may include, for example, a temperature sensor to determine the temperature of the downhole fluid, a densimeter to determine the density of a downhole fluid, and/or any other sensor(s) that may be useful to accurately determining the viscosity of the downhole fluid.

The example viscometer 500 of FIG. 5 and analyzer 512 of FIG. 6 have been tested on a certified reference fluid having a viscosity S60. Using a tungsten sensing wire having a nominal diameter of 0.25 mm, the viscosity was measured at temperatures between 273 K to 373° K (that is 0 to 100 C). The voltage generated by the AC signal source 506 and the pre-amplifier 508 was 5.0 volts AC (VAC) when the temperature T<293° K, 2.0 VAC when T=293° K, and 1.5 VAC when T>293° K. For each measurement, the resistance of the nulling circuit was changed to substantially equal the resistance of the sensing wire 502. The viscosity range of the fluid ranged from 6.2 mPa·s at T=273° K to 652.3 cP at T=373° K. Additionally, calibration measurements for the viscometer 500 using methylbenzene as the measured fluid showed viscosity measurements of 0.6 mPa·s. Thus, the example viscometer 500 may be used to measure viscosities ranging over three orders of magnitude, making the viscometer 500 very useful for general purpose downhole viscosity measurement. Further, none of the measured viscosities over the sample measured temperature range differed from the certified viscosity values by more than 3.5%.

Figure 7:
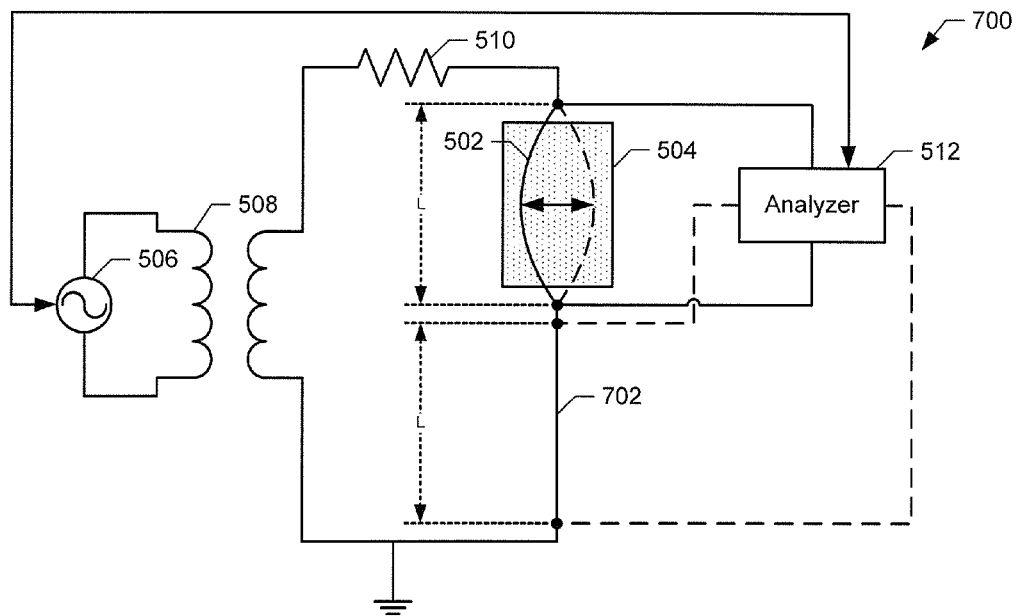
FIG. 7 is a schematic diagram of another example passive vibrating wire viscometer to extend the range of viscosity measurements.

FIG. 7 is a schematic diagram of another example passive vibrating wire viscometer 700 to extend the range of viscosity measurements. The example viscometer 700 may be used to implement the viscometer 60 of FIG. 3 to measure a viscosity of a downhole fluid. Like the example viscometer 500 of FIG. 5, the example viscometer 700 includes the sensing wire 502 exposed to the magnetic field 504, the AC signal generator 506, the transformer 508, the current-limiting resistor 510, and the analyzer 512. However, instead of the nulling circuit 514, the viscometer 700 includes an additional reference wire 702 made of the same material(s) and having the same length as the wire 502. Unlike the example of FIG. 5, the viscometer 700 does not need to be calibrated prior to measurements.

The example reference wire 702 is in series with the sensing wire 502 and, thus, the same current flows through both of the wires 502 and 702. By providing the same current to both of the wires 502 and 702, which have equal lengths and resistivities, the voltage drops across each of the wires 502 and 702 should be substantially equal. The reference wire 702 is not exposed to a magnetic field and, thus, does not vibrate (i.e., does not generate a motional emf $V_2$). Instead, the reference wire 702 provides a reference signal $V_1$ which may be measured by the analyzer 512 and subtracted from the signal $V=V_1+V_2$ across the sensing wire 502. In the example of FIG. 7, the analyzer 512 (e.g., via the lock-in amplifier 602 and the subtractor 610 of FIG. 6) measures the voltage signal across the sensing wire 502 and the voltage signal across the reference wire 702 simultaneously. The example lock-in amplifier 602 of FIG. 6 then passes the measurements to the subtractor 610, which subtracts the voltage signal across the reference wire 702 from the voltage signal across the sensing wire 502. The subtraction results in the motional emf or voltage $V_2$, which is passed from the subtractor 610 to the viscosity calculator 608. Using this method, the analyzer 512 may determine the motional emf $V_2$ on the sensing wire 502 and, thus, determine the viscosity of the downhole fluid using Equations 2 to 6 as described above.

Figure 8:
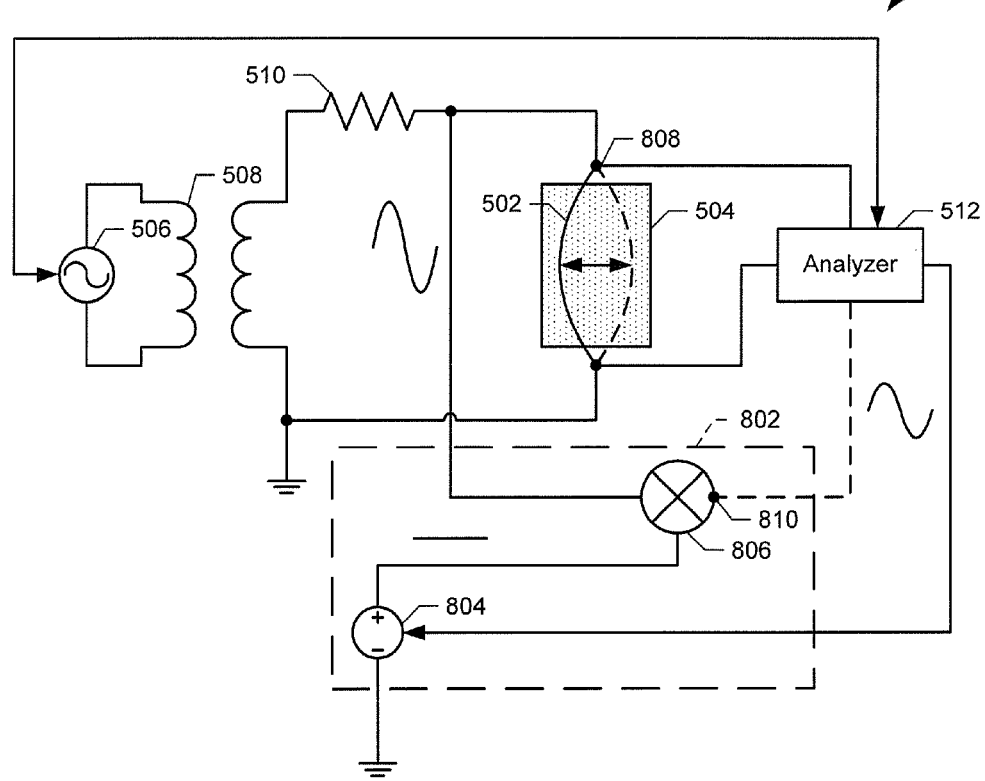
FIG. 8 is a schematic diagram of an example active vibrating wire viscometer to extend the range of viscosity measurements.

FIG. 8 is a schematic diagram of an example active vibrating wire viscometer 800 to extend the range of viscosity measurements. The example viscometer 800 may be used to implement the viscometer 60 of FIG. 3 to measure a viscosity of a downhole fluid. Like the example viscometer 500 of FIG. 5, the example viscometer 800 includes the sensing wire 502 exposed to the magnetic field 504, the AC signal generator 506, the transformer 508, the current-limiting resistor 510, and the analyzer 512. In contrast to the passive vibrating wire viscometers 500 and 700 illustrated in FIGS. 5 and 7, the example viscometer 800 includes electrically active components to establish an offset voltage corresponding to the voltage $V_1$ on the sensing wire 502. In particular, the viscometer 800 includes a nulling circuit 802 that includes a DC voltage source 804 and a multiplier 806. The active nulling circuit 802 provides a flexible method to nullify or offset $V_1$ by more precisely matching $V_1$ relative to the example of FIG. 5.

To generate the offset voltage, the example analyzer 512 conducts a test measurement of the offset voltage at a test frequency different than the resonance frequency of the sensing wire 502 similar to the test described above in connection with FIG. 5. That is, the frequency controller 604 (FIG. 6) adjusts the measurement frequency range of the lock-in amplifier 602 (FIG. 6), which receives the test frequency and measures the offset voltage $V_1$ at the measurement point(s).

In the example of FIG. 8, the lock-in amplifier 602 of FIG. 6 receives a measurement from node 808 with respect to the ground reference (i.e., the voltage across the sensing wire 502). The analyzer 512 (e.g., via the offset controller 606) adjusts the offset voltage of the DC offset generator 804. The DC offset generator 804 then outputs a DC signal based on the offset voltage. The DC signal is multiplied by the AC signal applied to the sensing wire 502 via the multiplier 806. As a result, the output signal from the multiplier 806 is equal to the offset voltage $V_1$ on the sensing wire 502. The analyzer 512 (e.g., via the lock-in amplifier 602 and/or the offset controller 606) may determine the output of the DC offset generator 804 by, for example, dividing the test voltage across the sensing wire 502 by the supply voltage during measurement. The division yields a DC signal that may be used to configure the DC offset generator 804. In some examples, the nulling circuit 802 may further include one or more amplifiers to amplify the AC and/or the DC input signal(s) to the multiplier 806.

After determining the offset voltage $V_1$ and configuring the DC offset generator 804, the analyzer 512 conducts a measurement by measuring the signal V at the sensing wire 502 at the resonance frequency and subtracting the offset voltage $V_1$ measured at the output of the multiplier 806 or the node 810. As mentioned above, the lock-in amplifier 602 may perform the measurements and pass the measured signal at the sensing wire 502 and the offset voltage $V_1$ to the subtractor 610 (FIG. 6). The subtractor 610 subtracts the offset voltage $V_1$ from the signal measured at the node 808 and sends the result of the subtraction to the viscosity calculator 608. The viscosity calculator 608 then determines the viscosity of the measured downhole fluid based on, for example, Equations 2 to 6.

Figure 9:
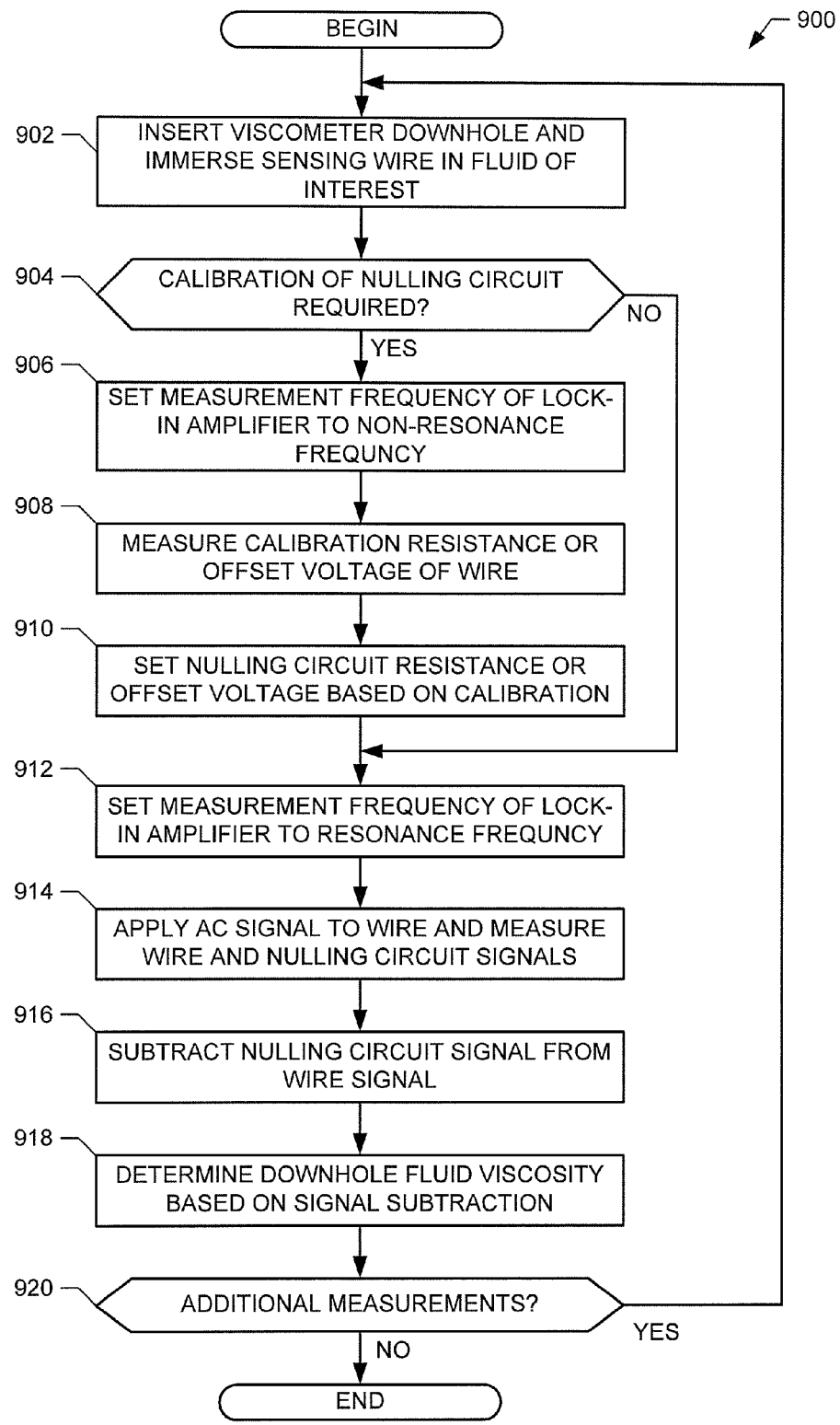
FIG. 9 is a flowchart representative of an example process that may be implemented to measure the viscosity of a downhole fluid.

FIG. 9 is a flowchart representative of an example process 900 that may be implemented to measure the viscosity of one or more downhole fluid samples. The process 900 may be used to implement the example viscometer 60 of FIG. 3. The example process 900 may begin by inserting a vibrating wire viscometer (e.g., one of the viscometers 500, 700, and/or 800 of FIGS. 5, 7, and/or 8) downhole and immersing a sensing wire (e.g., the sensing wire 502 of FIGS. 5, 7, and/or 8) within a downhole fluid of interest (block 902). The inserted viscometer 500, 700, or 800 includes a nulling circuit (e.g., one of the nulling circuits 514, 702, or 802). The process 900 then determines whether calibration of the nulling circuit is required (block 904). For example, the example nulling circuits 514 and/or 802 may need to be calibrated prior to measuring the viscosity of the downhole fluid sample. In contrast, the reference wire 702 (FIG. 7) does not need to be calibrated prior to measurement.

If the nulling circuit needs to be calibrated (block 904), the process 900 (e.g., via the frequency controller 604 of FIG. 6) sets the measurement frequency range of a lock-in amplifier (e.g., the lock-in amplifier 602 of FIG. 6) to a frequency that is not the resonance frequency of the sensing wire 502 (block 906). The example process 900 (e.g., via the analyzer 512 of FIGS. 5, 6, 7, and/or 8) measures the appropriate resistance and/or offset voltage of the sensing wire 502 as a signal generator (e.g., the AC signal generator 506 of FIGS. 5, 6, and 8) applies the AC signal to the wire 502 (block 908). For example, the analyzer 512 may measure the resistance of the sensing wire 502 if using the nulling circuit 514 of FIG. 5. In contrast, the analyzer 512 may measure the offset voltage of the wire 502 if using the example nulling circuit 802 of FIG. 8. Of course, the offset voltage and the resistance may each be calculated by measuring the other.

Based on the measured resistance and/or offset voltage (block 908), the analyzer 514 (e.g., via the offset controller 506) sets the resistance and/or offset voltage of the nulling circuit 514 or 802 (block 910). For example, the offset controller 606 may adjust the resistance value of the potentiometer 520 of FIG. 5 or may adjust the offset voltage of the voltage source 806.

After configuring the nulling circuit resistance and/or offset voltage (block 910), or if calibration of the nulling circuit is not required (block 904), the analyzer 514 sets the frequency of lock-in amplifier 602 to the resonance frequency (block 912). The AC signal generator applies or continues to apply the AC signal to the sensing wire 502 in the presence of a magnetic field (e.g., the magnetic field 504 of FIGS. 5, 7, and/or 8) causes the sensing wire 502 to vibrate, which causes a motional emf (e.g., $V_2$) based on the viscosity of the downhole fluid as the analyzer 512 (e.g., via the lock-in amplifier 602) measures the resulting signals at the sensing wire 502 and at the nulling circuit 514, 702, or 802 (block 914).

Based on the measurements (block 914), the analyzer 512 (e.g., via the subtractor 610) subtracts the signal at the nulling circuit 514, 702, or 802 from the signal at the sensing wire 502 (block 916). In some examples, block 916 may be omitted based on the configuration measurement reference of the lock-in amplifier 602. For example, block 916 may be omitted or skipped if the analyzer 512 is configured to measure the signal at node 522 with reference to node 524 as illustrated in FIG. 5.

The analyzer 512 (e.g., via the viscosity calculator 608) then determines the viscosity of the downhole fluid based on the signal subtraction (if necessary) (block 918). For example, the viscosity calculator 608 may solve the example Equations 2 to 6 for the fluid viscosity η. After determining the viscosity (block 918), the example process 900 may determine whether to take additional measurements of the same or different downhole fluid samples (block 920). If additional measurements are required, control returns to block 902 to immerse the sensing wire 502 in a downhole fluid sample. Additionally, the nulling circuit may need to be recalibrated at blocks 906-910 for different downhole conditions. If no more measurements are to be taken (block 920), the example process 900 may end.

While some example circuit values (e.g., resistances), frequencies, materials, and measurement results are provided herein, the resistances, frequencies, and materials may be modified without departing from the scope of this disclosure. For example, the diameter of the sensing wire 502 used in the described sample tests may be further increased to increase the upper viscosity range of the example viscometers within the limits of the quality factor as described above. Similarly, different current-limiting resistance values, AC current signals, and/or pre-amplifiers may be used to increase measurement accuracy when a particular range of viscosities are expected to be measured. In general, the example viscometers described herein can measure downhole fluids having viscosities up to and greater than 600 cP.

Additionally, while the foregoing description refers to the resonance frequency as a known value, the measurement frequency may be swept during measurement if the resonance frequency of a sensing wire is not known.

Although example methods, apparatus and articles of manufacture have been described herein, the scope of coverage of this patent is not limited thereto. On the contrary, this patent covers every apparatus, method and article of manufacture fairly falling within the scope of the appended claims either literally or under the doctrine of equivalents.

What is claimed is:

1. An apparatus to determine the viscosity of a downhole fluid, comprising:
    a wire to be immersed in a downhole fluid, to vibrate when an alternating current is applied to the wire within a magnetic field, and to generate an electromotive force when vibrating within the magnetic field, the wire comprising a first resistance;
    a nulling circuit coupled to the wire, wherein the nulling circuit comprises a second resistance that is selectable to be substantially equal to the first resistance; and
    an analyzer coupled to the wire and the nulling circuit to determine the first resistance, the second resistance, and a viscosity of the downhole fluid based on the first and second resistances, at least one characteristic of the wire, and the electromotive force.

2. An apparatus as defined in claim 1, wherein the analyzer comprises a lock-in amplifier to determine the viscosity of the downhole fluid by determining an induced voltage at the wire relative to the nulling circuit.

3. An apparatus as defined in claim 1, wherein the analyzer further comprises a subtractor to subtract a first signal at the nulling circuit from a second signal at the wire.

4. An apparatus as defined in claim 1, wherein the analyzer further comprises a viscosity calculator.

5. An apparatus as defined in claim 1, wherein the analyzer further comprises an offset controller to configure the nulling circuit based on an induced voltage.

6. An apparatus as defined in claim 1, wherein the nulling circuit comprises a first resistive element having a fixed resistance and a second resistive element having a variable resistance to provide the selectable second resistance.

7. An apparatus as defined in claim 1, wherein the nulling circuit comprises a second wire coupled in series with the wire to be immersed in the downhole fluid, the second wire having a resistance length substantially equal to the wire.

8. An apparatus as defined in claim 1, wherein the downhole fluid has a viscosity greater than 600 mPa·s.

9. An apparatus as defined in claim 1, wherein the wire provides a quality factor greater than or equal to 1.5.

10. An apparatus to determine the viscosity of a downhole fluid, comprising:
    a wire to be immersed in a downhole fluid, to vibrate when an alternating current is applied to the wire within a magnetic field, and to generate an electromotive force when vibrating within the magnetic field, the wire comprising a resistance;
    a nulling circuit coupled to the wire to generate an offset signal; and
    an analyzer coupled to the wire and the nulling circuit to determine an offset voltage based on the resistance, to configure the offset signal based on the offset voltage, and to determine a viscosity of the downhole fluid based on the resistance, the offset signal, at least one characteristic of the wire, and the electromotive force.

11. An apparatus as defined in claim 10, wherein the nulling circuit comprises a direct current signal generator to generate the offset signal and a multiplier to multiply the offset signal with a second signal based on the alternating current.

12. An apparatus as defined in claim 10, wherein the analyzer comprises a lock-in amplifier to determine the viscosity of the downhole fluid by determining an induced voltage at the wire relative to the nulling circuit.

13. An apparatus as defined in claim 12, wherein the analyzer further comprises an offset controller to configure the signal generator based on the induced voltage.

14. A method to measure a viscosity of a downhole fluid, comprising:
    immersing a wire in a downhole fluid;
    determining at least one of a resistance or an offset voltage on the wire;
    configuring a nulling circuit to compensate for the resistance or the offset voltage;
    applying an alternating current to the wire to cause the wire to vibrate a resonance frequency and generate an electromotive force while the wire is subjected to a magnetic field; and
    determining a voltage on the wire during vibration of the wire by determining a difference between a first signal generated by the alternating current and the magnetic field at the wire and a second signal generated by the nulling circuit.

15. A method as defined in claim 14, wherein determining the difference between the first and second signals comprises subtracting the second signal from the first signal.

16. A method as defined in claim 14, wherein determining the difference between the first and second signals comprises determining the first signal based on the second signal.

17. A method as defined in claim 14, wherein configuring the nulling circuit comprises measuring the resistance of the wire and adjusting a resistance of the nulling circuit to be substantially equal to the resistance of the wire.

18. A method as defined in claim 17, wherein adjusting the resistance of the nulling circuit comprises adjusting a variable resistance in parallel with a fixed resistance.

19. A method as defined in claim 14, wherein configuring the nulling circuit comprises measuring an offset voltage of the wire and configuring an offset signal generator to output a nulling signal based on the offset voltage.

20. A method as defined in claim 19, further comprising generating the second signal by multiplying the nulling signal by a third signal based on the alternating current.

* * * * *